United States Patent
Noh et al.

(10) Patent No.: US 12,397,179 B2
(45) Date of Patent: Aug. 26, 2025

(54) ULTRASONIC TRANSDUCER POSITIONING APPARATUS, ULTRASONIC TRANSDUCER POSITIONING PROGRAM, AND ULTRASONIC TRANSDUCER POSITIONING ARTIFICIAL-INTELLIGENCE IMPLEMENTATION METHOD

(71) Applicant: KOREA UNIVERSITY RESEARCH AND BUSINESS FOUNDATION, Seoul (KR)

(72) Inventors: Gun Woo Noh, Daegu (KR); Kyung Ho Yoon, Seoul (KR); Min Yeong Jang, Seoul (KR); Min Wook Choi, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 18/722,555

(22) PCT Filed: May 10, 2022

(86) PCT No.: PCT/KR2022/006608
§ 371 (c)(1),
(2) Date: Jun. 20, 2024

(87) PCT Pub. No.: WO2023/120827
PCT Pub. Date: Jun. 29, 2023

(65) Prior Publication Data
US 2025/0041629 A1    Feb. 6, 2025

(30) Foreign Application Priority Data
Dec. 20, 2021 (KR) .......... 10-2021-0182937

(51) Int. Cl.
*A61N 7/00* (2006.01)
*G16H 20/40* (2018.01)
*G16H 40/60* (2018.01)

(52) U.S. Cl.
CPC .............. *A61N 7/00* (2013.01); *G16H 20/40* (2018.01); *G16H 40/60* (2018.01); *A61N 2007/0026* (2013.01)

(58) Field of Classification Search
CPC .............. A61N 7/00; A61N 2007/0026; A61N 2007/0095; A61N 7/02; A61N 2007/0056;
(Continued)

(56) References Cited

FOREIGN PATENT DOCUMENTS

| JP | 2015-521490 A | 7/2015 |
|----|---------------|--------|
| JP | 2019-509871 A | 4/2019 |

(Continued)

OTHER PUBLICATIONS

Benjdira, Bilel, et al. "Spinal cord segmentation in ultrasound medical imagery." Applied Sciences 10.4, 1370, Feb. 18, 2020. (pp. 1-24).

(Continued)

*Primary Examiner* — Joel Lamprecht
(74) *Attorney, Agent, or Firm* — NSIP Law (57) ABSTRACT

The present invention relates to an ultrasonic transducer position setting device, an ultrasonic transducer position setting program, and a method for implementing ultrasonic transducer position setting artificial intelligence. The ultrasonic transducer position setting device includes: an input/output unit for allowing a user to input data, and outputting the data in a form that is recognizable by the user; a memory for storing an ultrasonic transducer position setting program; and a control unit for executing the ultrasonic transducer position setting program to derive result data according to the data input through the input/output unit, wherein, when (Continued)

a focal point position of ultrasound, which is set to a region where a brain is positioned inside a skull in a living body, is input, the control unit outputs position data of an ultrasonic transducer, which allows the ultrasound to be applied to the input focal point position of the ultrasound.

13 Claims, 8 Drawing Sheets

(58) Field of Classification Search
CPC ........... A61N 2007/0091; G16H 20/40; G16H 40/60; A61B 2034/101; A61B 2034/107; A61B 34/10
See application file for complete search history.

(56) References Cited

FOREIGN PATENT DOCUMENTS

| JP | 2020-533103 A | 11/2020 |
|----|---------------|---------|
| KR | 10-2019-0060606 A | 6/2019 |
| KR | 2019-0108286 A | 9/2019 |
| KR | 10-2144671 B1 | 8/2020 |
| KR | 10-2245150 B1 | 4/2021 |
| KR | 10-2250219 B1 | 5/2021 |

OTHER PUBLICATIONS

Choi, Minwook, et al. "Deep neural network for navigation of a single-element transducer during transcranial focused ultrasound therapy: proof of concept." IEEE Journal of Biomedical and Health Informatics 26.11, Nov. 2022. (pp. 5653-5664).

Wang, Liansheng, Cong Xie, and Nianyin Zeng. "RP-Net: a 3D convolutional neural network for brain segmentation from magnetic resonance imaging." IEEE Access 7, Apr. 8, 2019. (pp. 39670-39679).

Yoo, Seung-Schik, et al. "Focused ultrasound modulates region-specific brain activity." Neuroimage 56.3 (2011): 1267-1275.

Chen, Liang-Chieh, et al. "DeepLab: Semantic image segmentation with deep convolutional nets, atrous convolution, and fully connected CRFs." IEEE transactions on pattern analysis and machine intelligence 40.4 (2017): 834-848.

ULTRASONIC TRANSDUCER POSITIONING APPARATUS, ULTRASONIC TRANSDUCER POSITIONING PROGRAM, AND ULTRASONIC TRANSDUCER POSITIONING ARTIFICIAL-INTELLIGENCE IMPLEMENTATION METHOD

CROSS REFERENCE TO RELATED APPLICATIONS

This application is a U.S. National Stage Application of International Application No. PCT/KR2022/006608, filed on May 10, 2022 which claims the benefit under 35 USC 119(a) and 365(b) of Korean Patent Application No. 10-2021-0182937, filed on Dec. 20, 2021, in the Korean Intellectual Property Office, the entire disclosure of which is incorporated herein by reference for all purposes.

TECHNICAL FIELD

The present invention relates to an ultrasonic transducer position setting device, an ultrasonic transducer position setting program, and a method for implementing ultrasonic transducer position setting artificial intelligence, and more particularly, to an ultrasonic transducer position setting device, an ultrasonic transducer position setting program, and a method for implementing ultrasonic transducer position setting artificial intelligence, capable of guiding a position of an ultrasonic transducer so that ultrasound is applied to a focal point position to which the ultrasound is intended to be applied.

BACKGROUND ART

Since focused ultrasound (FUS) may perform a medical treatment noninvasively by emitting acoustic energy concentrated in a local region within a biological tissue, the focused ultrasound is used for treatments in various regions. For a noninvasive treatment using the focused ultrasound, the ultrasound has to be capable of being emitted to a desired region. However, the ultrasound is invisible, and exhibits reflection and refraction characteristics when transmitted to a tissue in a living body.

In order to solve the above problem, a magnetic-resonance-guided focused ultrasound (MRgFUS) system for identifying a temperature variation through magnetic resonance to visualize ultrasound has been developed. However, the MRgFUS system has a problem that a procedure requires a long time. In addition, in a case of a transcranial treatment, low-intensity focused ultrasound is mainly used, and it is difficult to use the magnetic-resonance-guided focused ultrasound system because a temperature variation is relatively small in the low-intensity focused ultrasound.

In addition, there is a system for displaying a focal point position of an ultrasonic transducer on a medical image that is acquired in advance by using a real-time optical tracking device through image-guided focused ultrasound (neuro-navigation). However, the system has a limitation that an effect of variations in the focal point position and intensity caused by a skull may not be taken into consideration.

DISCLOSURE

Technical Problem

An object of the present invention is to provide an ultrasonic transducer position setting device, an ultrasonic transducer position setting program, and a method for implementing ultrasonic transducer position setting artificial intelligence, capable of guiding a position of an ultrasonic transducer so that ultrasound is applied to a focal point position to which the ultrasound is intended to be applied.

In addition, an object of the present invention is to provide an ultrasonic transducer position setting device, an ultrasonic transducer position setting program, and a method for implementing ultrasonic transducer position setting artificial intelligence, capable of guiding a position of an ultrasonic transducer, which enables ultrasound to be concentrated at a desired position, by reflecting refraction that occurs when the ultrasound passes through a skull.

In addition, an object of the present invention is to provide an ultrasonic transducer position setting device, an ultrasonic transducer position setting program, and a method for implementing ultrasonic transducer position setting artificial intelligence, capable of guiding a position of an ultrasonic transducer at a speed close to a real time with high accuracy.

Technical Solution

According to one aspect of the present invention, there is provided an ultrasonic transducer position setting device including: an input/output unit for allowing a user to input data, and outputting the data in a form that is recognizable by the user; a memory for storing an ultrasonic transducer position setting program; and a control unit for executing the ultrasonic transducer position setting program to derive result data according to the data input through the input/output unit, wherein, when a focal point position of ultrasound, which is set to a region where a brain is positioned inside a skull in a living body, is input, the control unit outputs position data of an ultrasonic transducer, which allows the ultrasound to be applied to the input focal point position of the ultrasound.

In addition, the control unit may output the position data of the ultrasonic transducer, which enables the ultrasound to be concentrated at the input focal point position, by reflecting that refraction occurs as the ultrasound passes through the skull.

In addition, the position data of the ultrasonic transducer may include coordinate data representing three-dimensional coordinates at which the ultrasonic transducer is positioned with respect to the skull, and angle data representing an angle at which the ultrasonic transducer is positioned with respect to the skull.

In addition, the ultrasonic transducer position setting program may be provided by artificial intelligence based on a deep neural network (DNN).

In addition, the ultrasonic transducer position setting program may include: a feature map training unit for training a feature map from the input data; and a coordinate training unit for training a relation between the feature map and the position data of the ultrasonic transducer.

In addition, the feature map training unit may include at least one modified atrous spatial pyramid pooling module.

In addition, the modified atrous spatial pyramid pooling module may include: a first convolutional network layer; a second convolutional network layer connected to an output terminal of the first convolutional network layer; and a max pooling layer connected to an output terminal of the second convolutional network layer.

In addition, the first convolutional network layer may include four convolutional networks connected in parallel to each other.

In addition, the second convolutional network layer may include four convolutional networks connected in parallel to each other.

In addition, the feature map training unit may include: a first modified atrous spatial pyramid pooling module; a second modified atrous spatial pyramid pooling module connected to an output terminal of the first modified atrous spatial pyramid pooling module; and a third modified atrous spatial pyramid pooling module connected to an output terminal of the second modified atrous spatial pyramid pooling module.

In addition, the first modified atrous spatial pyramid pooling module, the second modified atrous spatial pyramid pooling module, and the third modified atrous spatial pyramid pooling module may have mutually different dilation rates of convolutional networks.

In addition, the artificial intelligence may use training data including shape data of the skull, the position data of the ultrasonic transducer, and acoustic pressure field shape data to perform training so as to predict the position data of the ultrasonic transducer according to the acoustic pressure field shape data by using the acoustic pressure field shape data as an input and using the position data of the ultrasonic transducer corresponding to the input as an output.

In addition, the training data may be generated through a simulation based on computational mechanics.

According to another aspect of the present invention, there is provided an ultrasonic transducer position setting program, wherein the ultrasonic transducer position setting program is stored in a recording medium that is readable by an ultrasonic transducer position setting device in order to allow the ultrasonic transducer position setting device to execute: inputting a focal point position of ultrasound, which is set to a region where a brain is positioned inside a skull in a living body; and outputting position data of an ultrasonic transducer, which allows the ultrasound to be applied to the input focal point position of the ultrasound.

In addition, the position data of the ultrasonic transducer may include coordinate data representing three-dimensional coordinates at which the ultrasonic transducer is positioned with respect to the skull, and angle data representing an angle at which the ultrasonic transducer is positioned with respect to the skull.

According to still another aspect of the present invention, there is provided a method for implementing ultrasonic transducer position setting artificial intelligence, which is provided by an ultrasonic transducer position setting program stored in a recording medium that is readable by an ultrasonic transducer position setting device, the method including: preparing training data including shape data of a skull, position data of an ultrasonic transducer, and acoustic pressure field shape data; and allowing artificial intelligence to perform training so as to predict the position data of the ultrasonic transducer according to the acoustic pressure field shape data by using the acoustic pressure field shape data as an input and using the position data of the ultrasonic transducer corresponding to the input as an output in the training data.

Advantageous Effects

According to one embodiment of the present invention, an ultrasonic transducer position setting device, an ultrasonic transducer position setting program, and a method for implementing ultrasonic transducer position setting artificial intelligence, capable of guiding a position of an ultrasonic transducer so that ultrasound is applied to a focal point position to which the ultrasound is intended to be applied, can be provided.

In addition, according to one embodiment of the present invention, an ultrasonic transducer position setting device, an ultrasonic transducer position setting program, and a method for implementing ultrasonic transducer position setting artificial intelligence, capable of guiding a position of an ultrasonic transducer, which enables ultrasound to be concentrated at a desired position, by reflecting refraction that occurs when the ultrasound passes through a skull, can be provided.

In addition, according to one embodiment of the present invention, an ultrasonic transducer position setting device, an ultrasonic transducer position setting program, and a method for implementing ultrasonic transducer position setting artificial intelligence, capable of guiding a position of an ultrasonic transducer at a speed close to a real time with high accuracy, can be provided.

MODE FOR INVENTION

Hereinafter, exemplary embodiments of the present invention will be described in detail with reference to the accompanying drawings. However, the technical idea of the present invention is not limited to the embodiments described herein, but may be realized in different forms. The embodiments introduced herein are provided to sufficiently deliver the idea of the present invention to those skilled in the art so that the disclosed contents may become thorough and complete.

When it is mentioned in the present disclosure that one element is on another element, it means that one element may be directly formed on another element, or a third element may be interposed between one element and another element. Further, in the drawings, thicknesses of films and regions are exaggerated for effective description of the technical contents.

In addition, in various embodiments of the present disclosure, the terms such as first, second, and third are used to describe various elements, but the elements are not limited by the terms. The terms are used only to distinguish one element from another element. Therefore, an element mentioned as a first element in one embodiment may be mentioned as a second element in another embodiment. The embodiments described and illustrated herein include their complementary embodiments. Further, the term "and/of" used herein is used to include at least one of the elements enumerated before and after the term.

As used herein, expressions in a singular form include a meaning of a plural form unless the context clearly indicates otherwise. Further, the terms such as "including" and "having" are intended to designate the presence of features, numbers, steps, elements, or combinations thereof described in the present disclosure, and shall not be construed to preclude any possibility of the presence or addition of one or more other features, numbers, steps, elements, or combinations thereof. In addition, the term "connection" used herein is used to include both indirect and direct connections of a plurality of elements.

Further, in the following description of the present invention, detailed descriptions of known functions or configurations incorporated herein will be omitted when they may make the gist of the present invention unnecessarily unclear.

Figure 1:
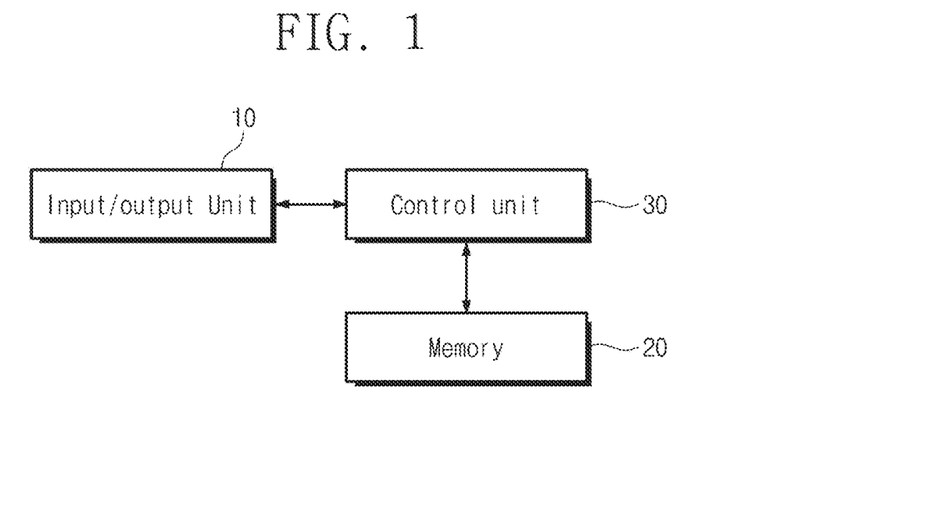
FIG. 1 is a view showing an ultrasonic transducer position setting device according to one embodiment of the present invention.

FIG. 1 is a view showing an ultrasonic transducer position setting device according to one embodiment of the present invention.

Referring to FIG. 1, according to one embodiment of the present invention, an ultrasonic transducer position setting device may include an input/output unit 10, a memory 20, and a control unit 30.

The input/output unit 10 may allow a user to input data, and output the data in a form that is recognizable by the user. For example, the input/output unit 10 may be provided as a keyboard, a mouse, a digitizing pad, or the like for allowing a user to input data. In addition, the input/output unit 10 may include a display panel and the like for outputting the data. In addition, the input/output unit 10 may be provided as a touch screen in which an input portion and an output portion are integrated. In addition, the input/output unit 10 may be provided in a form in which a portion for inputting data or a portion for outputting data is integrated with another medical device, so that the medical device may input the data or output the data.

The memory 20 may store the data. The memory 20 may be provided such that an ultrasonic transducer position setting program is stored therein. In this case, the ultrasonic transducer position setting program may be implemented based on artificial intelligence. In detail, the ultrasonic transducer position setting program may be implemented by artificial intelligence based on a deep neural network (DNN). In addition, the memory 20 may store the data input through the input/output unit 10 and data generated by applying the data input through the input/output unit 10 to the ultrasonic transducer position setting program.

The control unit 30 may execute the ultrasonic transducer position setting program stored in the memory 20 to derive result data according to the data input through the input/output unit 10 and output the derived result data through the input/output unit 10.

Figure 2:
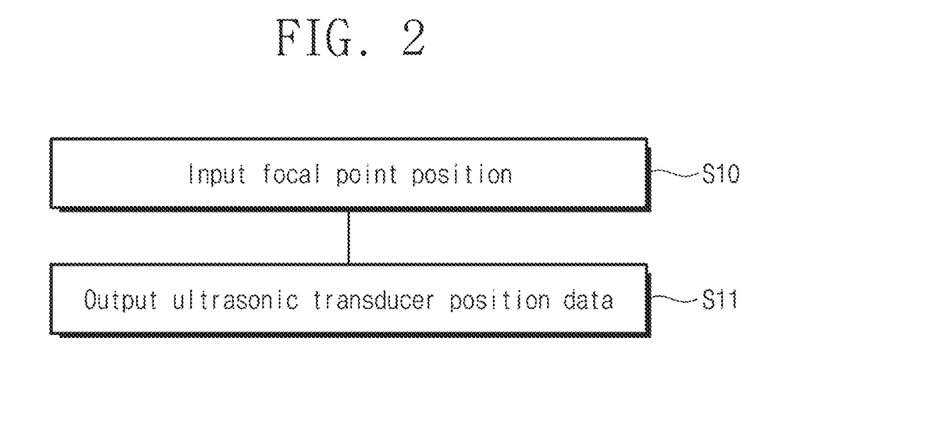
FIG. 2 is a view showing a process of deriving result data by the ultrasonic transducer position setting device according to one embodiment of the present invention.

FIG. 2 is a view showing a process of deriving result data by the ultrasonic transducer position setting device according to one embodiment of the present invention.

Referring to FIG. 2, according to one embodiment of the present invention, the ultrasonic transducer position setting device may, when a focal point position of ultrasound is input (S10), output position data of an ultrasonic transducer, which allows the ultrasound to be applied to the input focal point position of the ultrasound (S11). In this case, the focal point position of the ultrasound may be set to a region where a brain is positioned inside a skull in a living body. Accordingly, the position data of the ultrasonic transducer may be provided as position data on an outer side of a head of the living body. Accordingly, when the ultrasound is applied while the ultrasonic transducer is positioned at a position corresponding to the output position data of the ultrasonic transducer, the ultrasound may be concentrated at the input focal point position.

Focused ultrasound (FUS) may emit acoustic energy concentrated in a local region within a biological tissue. Accordingly, the focused ultrasound has been used for purposes such as diagnosis and a treatment by applying energy to an inside of a human body. In particular, it has been confirmed that the focused ultrasound may stimulate the brain noninvasively when applied to the brain, so that the focused ultrasound may be used for brain stimulation and treatments.

The focused ultrasound may be divided into high-intensity focused ultrasound (HIFU) and low-intensity focused ultrasound (LIFU) depending on intensity. Similar to thrombolysis, extracorporeal shockwaves, thermal ablation, boiling histotripsy, and the like, the high-intensity focused ultrasound may directly change a condition of a target region to produce a treatment effect.

Meanwhile, the low-intensity focused ultrasound may be used in fields such as drug delivery through opening of a blood-brain barrier and noninvasive brain stimulation. In addition, the low-intensity focused ultrasound has recently been found to be effective in treating neurological diseases such as epilepsy, brain tumors, an Alzheimer's disease, and a Parkinson's disease.

In order for a treatment with the focused ultrasound to be effective, the ultrasound has to be capable of being emitted to a desired region. However, the ultrasound is invisible, and exhibits reflection and refraction characteristics when traveling in the living body. In particular, the ultrasound may have distortion when passing through a boundary at which regions with mutually different physical properties meet due to wave characteristics, so that severe distortion may occur when the ultrasound passes through the skull or a porous region. Accordingly, it is difficult to use the ultrasound for a transcranial treatment.

Meanwhile, according to one embodiment of the present invention, the ultrasonic transducer position setting device may provide a position of the ultrasonic transducer, which enables the ultrasound to be concentrated at a desired focal point position, by reflecting that refraction occurs as the ultrasound travels and passes through regions including the skull. Accordingly, the user who performs a medical practice may effectively perform the medical practice using the ultrasound by positioning the ultrasonic transducer at the position provided by the ultrasonic transducer position setting device.

Figure 3:
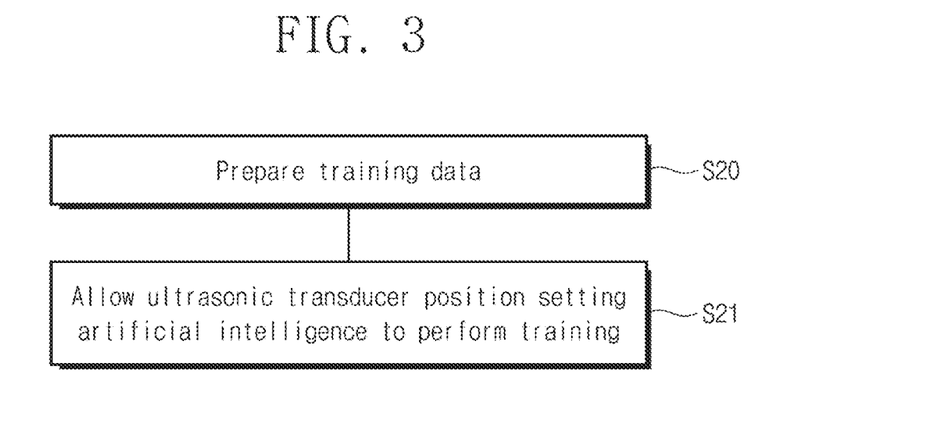
FIG. 3 is a flow chart showing a method for implementing ultrasonic transducer position setting artificial intelligence provided by an ultrasonic transducer position setting program according to one embodiment of the present invention.

FIG. 3 is a flow chart showing a method for implementing ultrasonic transducer position setting artificial intelligence provided by an ultrasonic transducer position setting program according to one embodiment of the present invention.

Referring to FIG. 3, training data for allowing ultrasonic transducer position setting artificial intelligence to perform training may be prepared (S20). The training data may include shape data of a skull, position data of an ultrasonic transducer, and acoustic pressure field shape data.

The shape data of the skull may be data on a three-dimensional shape of the skull. The shape data of the skull may be provided in the form of a three-dimensional image of the skull.

The position data of the ultrasonic transducer may be data on a point at which the ultrasonic transducer is positioned with respect to the skull. The position data of the ultrasonic transducer may include coordinate data representing three-dimensional coordinates at which the ultrasonic transducer is positioned with respect to the skull, and angle data representing an angle at which the ultrasonic transducer is positioned with respect to the skull (i.e., an angle at which the ultrasound is emitted with respect to the skull).

The acoustic pressure field shape data may be data on a shape in which the ultrasound emitted from the ultrasonic transducer travels inside the skull, that is, in a region where the brain is positioned. The acoustic pressure field shape data may be provided in the form of a three-dimensional image, a two-dimensional image for a specific reference plane, or the like. The acoustic pressure field shape data may be paired with the position data of the ultrasonic transducer. The acoustic pressure field shape data may be binarized into a focal point region and a focal point outside region of the ultrasound through a full-width-at-half-maximum (FWHM) threshold according to a definition of a focal point of the focused ultrasound, as will be described below. In addition, a boundary of the focal point region may be converted from a boundary based on the FWHM threshold into an ellipsoid boundary.

The training data may be acquired by positioning the ultrasonic transducer to be adjacent to the skull of the living body, and photographing a shape of the skull and a path in which the ultrasound travels through an existing medical device while emitting the ultrasound.

In addition, the training data may be acquired through a simulation based on computational mechanics.

Figure 4:
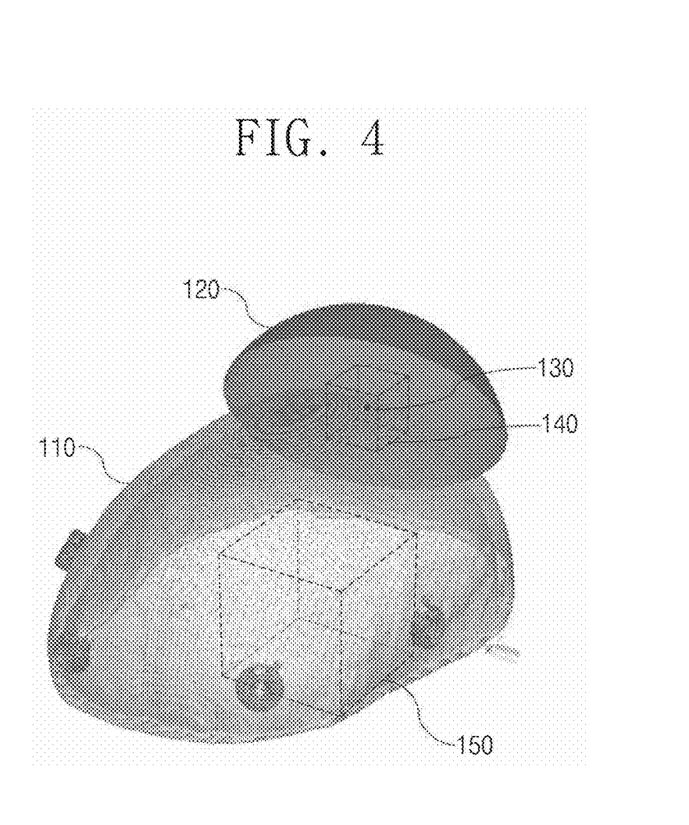
FIG. 4 is a view showing a configuration of data to acquire training data by performing a simulation based on computational mechanics.

FIG. 4 is a view showing a configuration of data to acquire training data by performing a simulation based on computational mechanics.

Referring to FIG. 4, data for numerical modeling of a simulation may include a skull model 110, an ultrasonic transducer model 120, and a region of interest 150.

The skull model 110 may correspond to the shape data of the skull of the training data. The skull model 110 may be provided by photographing an actual skull. For example, the skull model 110 may be provided by performing CT scanning on the actual skull. The skull model 110 may be provided with a set spatial resolution or more to have satisfactory precision and a satisfactory spatial resolution in water. For example, the skull model 110 may be provided by performing the CT scanning to have a spatial resolution of 0.5 mm×0.5 mm×0.5 mm or more. Voxels of the skull model 110 may be classified into water, a cancellous bone, and a cortical bone according to Hounsfield units ($\phi_{i,j,k}$), as shown in Mathematical Formula 1.

$$c_{i,j,k} = \begin{cases} 1500 \ m/s, & \text{for } \phi_{i,j,k} \leq 0 \\ 2140 \ m/s, & \text{for } 0 < \phi_{i,j,k} \leq 1000 \\ 2384 \ m/s, & \text{for } 1000 < \phi_{i,j,k} \end{cases} \quad \text{[Formula 1]}$$

$$\rho_{i,j,k} = \begin{cases} 1000 \ kg/m^3, & \text{for } \phi_{i,j,k} \leq 0 \\ 1000 + 1.19\phi_{i,j,k} \ kg/m^3, & \text{for } 0 < \phi_{i,j,k} \leq 1000 \\ 2190 \ kg/m^3, & \text{for } 1000 < \phi_{i,j,k} \end{cases}$$

$$a_{i,j,k} = 33 \ Np/m,$$

$$\text{for } 0 < \phi_{i,j,k}$$

$c_{i,j,k}$
is a velocity of ultrasound, and
$\rho_{i,j,k}$
is a density of ultrasound. In this case,
$\phi_{i,j,k} \leq 0$
is water,
$0 < \phi_{i,j,k} \leq 1000$
is a cancellous bone, and
$1000 < \phi_{i,j,k}$
is a cortical bone.
$a_{i,j,k}$
is an attenuation coefficient.

Figure 5:
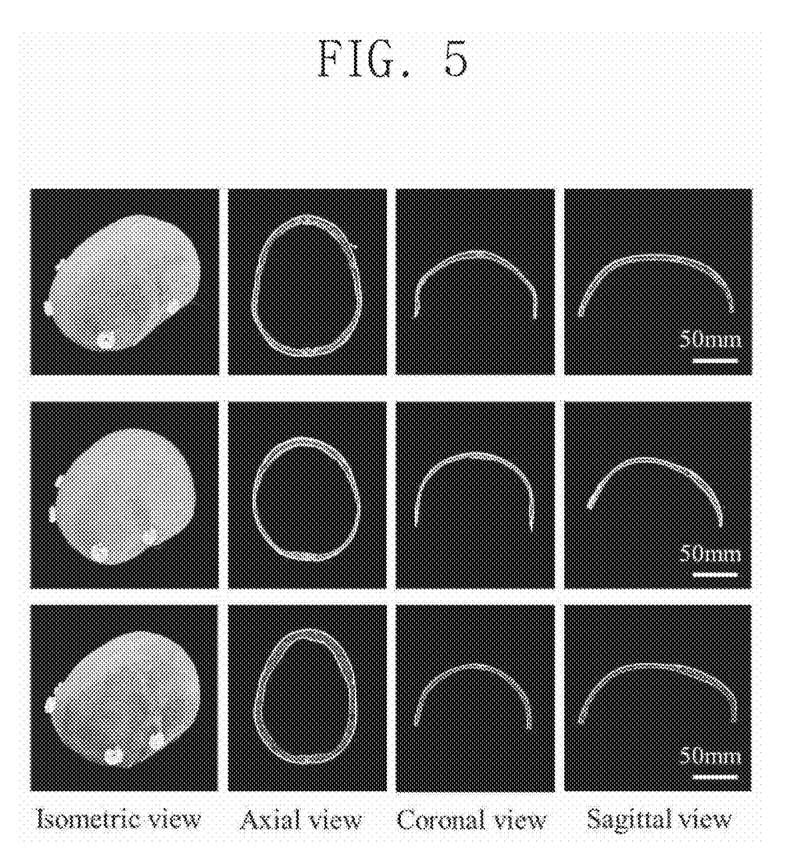
FIG. 5 is a view showing an actual skull provided to construct a skull model.

FIG. 5 is a view showing an actual skull provided to construct a skull model.

Referring to FIG. 5, a plurality of skull models 110 may be created by using at least two different actual skulls, respectively. FIG. 5 illustrates a case in which three different actual skulls are provided so that three skull models 110 are created by using the three different actual skulls, respectively.

The ultrasonic transducer model 120 may be acquired by modeling an actual ultrasonic transducer. The ultrasonic transducer model 120 may be modeled to have a preset diameter, a preset radius of curvature, and a preset focal length. For example, the ultrasonic transducer model 120 may be modeled to have a diameter of 96 mm, a radius of curvature of 52 mm, and a focal length of 83 mm. A position reference point 130 may be set in the ultrasonic transducer model 120, so that coordinates of the position reference point may be set as a position of the ultrasonic transducer model 120. For example, a central region of an exit surface facing the skull model 110 in the ultrasonic transducer model 120 may be set as the position reference point 130. Simulations may be performed while the position of the ultrasonic transducer model 120 varies in a movement region 140 that is adjacent to the skull model 110. The movement region 140 may be adjacent to an upper outer surface of the skull model 110, and may be set to have a preset volume. For example, the movement region 140 may be set to have a size of 20 mm×20 mm×20 mm.

The position of the ultrasonic transducer model 120 may include simulation coordinate data representing three-dimensional coordinates of the position reference point 130, and simulation angle data representing an angle at which the ultrasonic transducer model 120 is positioned with respect to the skull model 110. The simulation angle data may be defined as a normal vector of the exit surface. The simulation coordinate data and the simulation angle data may correspond to the coordinate data and the angle data of the ultrasonic transducer, respectively.

The region of interest 150 may be a region for acquiring data on a shape in which the ultrasound emitted from the ultrasonic transducer model 120 propagates, and may be set to have a preset volume. For example, the region of interest 150 may be set to have a size of 50 mm×50 mm×50 mm.

A center point of the region of interest 150 may be set at a position spaced apart from an initial position of the ultrasonic transducer model 120 by the focal length. A simulation for acquiring the shape in which the ultrasound propagates in the region of interest 150 may be performed while varying the position of the ultrasonic transducer model 120. In order to perform ultrasonic propagation modeling in the region of interest 150, the Westervelt-Lighthill equation as shown in [Mathematical Formula 2] may be used as a governing equation.

$$\nabla^2 p - \frac{1}{c^2}\frac{\partial^2 p}{\partial t^2} - \frac{\tilde{a}}{c^2}\frac{\partial p}{\partial t} = 0 \quad \text{[Formula 2]}$$

with $$\tilde{a} = 2a\sqrt{\frac{a^2 c^4}{4\pi^2 f^2} + c^2}$$

In this case, p is a pressure of sound, c is a wave velocity in a medium, a is an attenuation coefficient in a medium, f is a frequency of the sound, and t is a time.

A finite-difference time-domain (FDTD) method as shown in [Mathematical Formula 3] may be used to approximate partial derivatives of the governing equation with respect to a space and a time, and ultrasonic propagation may be performed by repeatedly evaluating the Formula.

$$^{t+\Delta t}P_{i,j,k} = {}^t P_{i,j,k} - C^p_{i,j,k}\left[({}^{t+1/2\Delta t}V^x_{i,j,k} - {}^{t+1/2\Delta t}V^x_{i-1,j,k}) + \right. \quad \text{[Formula 3]}$$

$$({}^{t+1/2\Delta t}V^y_{i,j,k} - {}^{t+1/2\Delta t}V^y_{i,j-1,k}) +$$

$$\left. ({}^{t+1/2\Delta t}V^z_{i,j,k} - {}^{t+1/2\Delta t}V^z_{i,j,k-1})\right] - A_{i,j,k}{}^t P_{i,j,k},$$

$${}^{t+1/2\Delta t}V^x_{i,j,k} = {}^{t-1/2\Delta t}V^x_{i,j,k} - C^{vx}_{i,j,k}[{}^t P_{i+1,j,k} - {}^t P_{i,j,k}],$$

$${}^{t+1/2\Delta t}V^y_{i,j,k} = {}^{t-1/2\Delta t}V^y_{i,j,k} - C^{vy}_{i,j,k}[{}^t P_{i,j+1,k} - {}^t P_{i,j,k}],$$

$${}^{t+1/2\Delta t}V^z_{i,j,k} = {}^{t-1/2\Delta t}V^z_{i,j,k} - C^{vz}_{i,j,k}[{}^t P_{1,j,k+1} - {}^t P_{i,j,k}],$$

$$C^p_{i,j,k} = \rho_{i,j,k} c^2_{i,j,k}\frac{\Delta t}{\delta},$$

$$A_{i,j,k} = 2\Delta t a_{i,j,k}\sqrt{\frac{a^2_{i,j,k}c^4_{i,j,k}}{4\pi^2 f^2} + c^2_{i,j,k}},$$

$$C^{vx}_{i,j,k} = \frac{2}{\rho_{i,j,k} + \rho_{i+1,j,k}}\frac{\Delta t}{\delta},$$

$$C^{vy}_{i,j,k} = \frac{2}{\rho_{i,j,k} + \rho_{i,j+1,k}}\frac{\Delta t}{\delta},$$

$$C^{vz}_{i,j,k} = \frac{2}{\rho_{i,j,k} + \rho_{i,j,k+1}}\frac{\Delta t}{\delta}.$$

In this case, $${}^t P_{i,j,k}$$

is an acoustic pressure value at a nodal point, $${}^t V_{i,j,k}^x,$$
$${}^t V_{i,j,k}^y,$$ and
$${}^t V_{i,j,k}^z$$

are velocities of a wave on x-, y-, and z-axes at a time t at a nodal point, respectively, $c_{i,j,k}$
is a velocity of ultrasound, $\rho_{i,j,k}$ is a density of ultrasound, and $a_{i,j,k}$ is an attenuation coefficient.

In this case, since an algorithm for solving explicit dynamic processes, including FDTD, has numerical errors, a stability condition known as the Courant-Friedrichs-Lewy (CFL) criterion, which may be expressed as [Mathematical Formula 4], has to be satisfied.

$$\Delta t \le \frac{\delta}{\sqrt{3}c} \quad \text{[Formula 4]}$$

In this case,
$\Delta t$
is a time interval,
$\delta$
is a discretized spatial interval, and c is a velocity.

Figure 6:
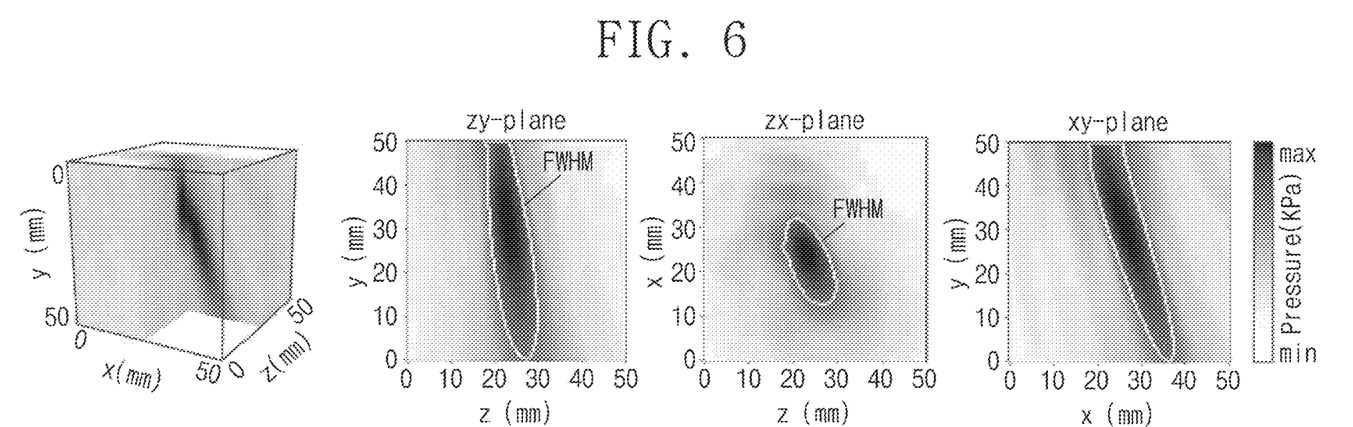
FIG. 6 is a view showing a result of expressing a propagation shape of ultrasound as acoustic pressure field shape data in a region of interest according to a result of the simulation.

FIG. 6 is a view showing a result of expressing a propagation shape of ultrasound as acoustic pressure field shape data in a region of interest according to a result of the simulation.

Referring to FIG. 6, when the simulation based on computational dynamics is performed, a pressure distribution of the ultrasound in the region of interest according to the position of the ultrasonic transducer model 120 may be acquired as the acoustic pressure field shape data. In this case, simulations may be performed on skull models 110 having mutually different shapes, respectively, to acquire results thereof.

Figure 7:
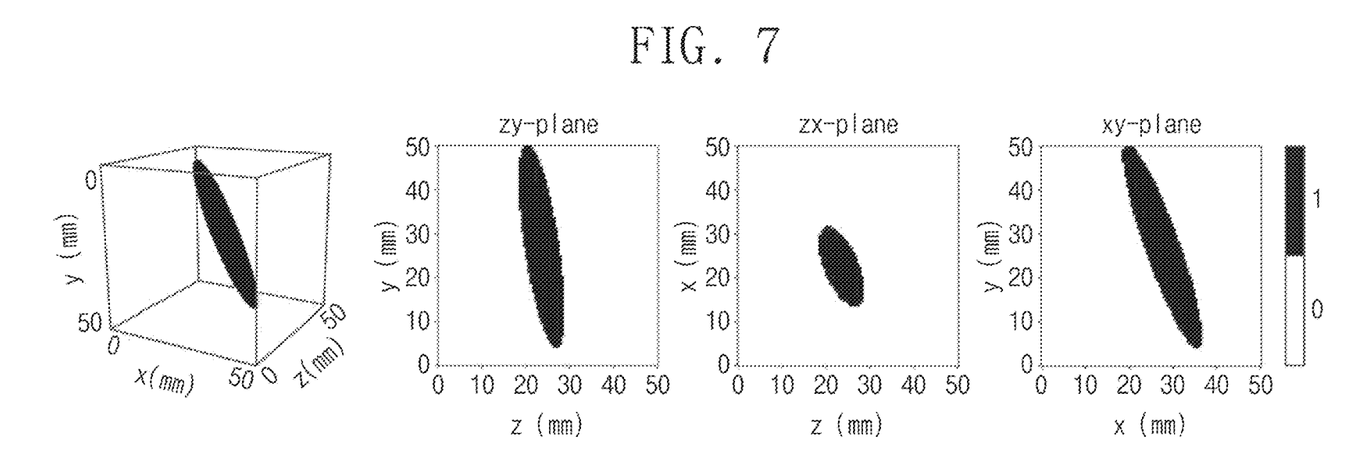
FIG. 7 is a view showing a result of binarizing an acoustic pressure field according to the result of the simulation.

FIG. 7 is a view showing a result of binarizing an acoustic pressure field according to the result of the simulation.

Referring to FIG. 7, a simulation result of an acoustic pressure field shape may be binarized into the focal point region and the focal point outside region of the ultrasound through the definition of the focal point of the focused ultrasound. The focal point region of the focused ultrasound may be defined as a region corresponding to the full-width-at-half-maximum (FWHM) threshold. When the simulation result is binarized, the boundary of the focal point region may have a non-linear shape that is complex and inconsistent. Accordingly, for training efficiency of the artificial intelligence, the simulation result provided as the training data according to one embodiment of the present invention may be configured such that the boundary of the focal point region is converted from the boundary according to the FWHM threshold into the ellipsoid boundary. In this case, the ellipsoid boundary may be set as an ellipsoid that is closest to the boundary according to the FWHM threshold. For example, the ellipsoid that is closest to the boundary according to the FWHM threshold may be formed by selecting an ellipse that includes or surrounds contour points on the boundary according to the FWHM threshold, such as the CV:fitEllipse function of the open source computer vision (OpenCV) library.

Figure 8:
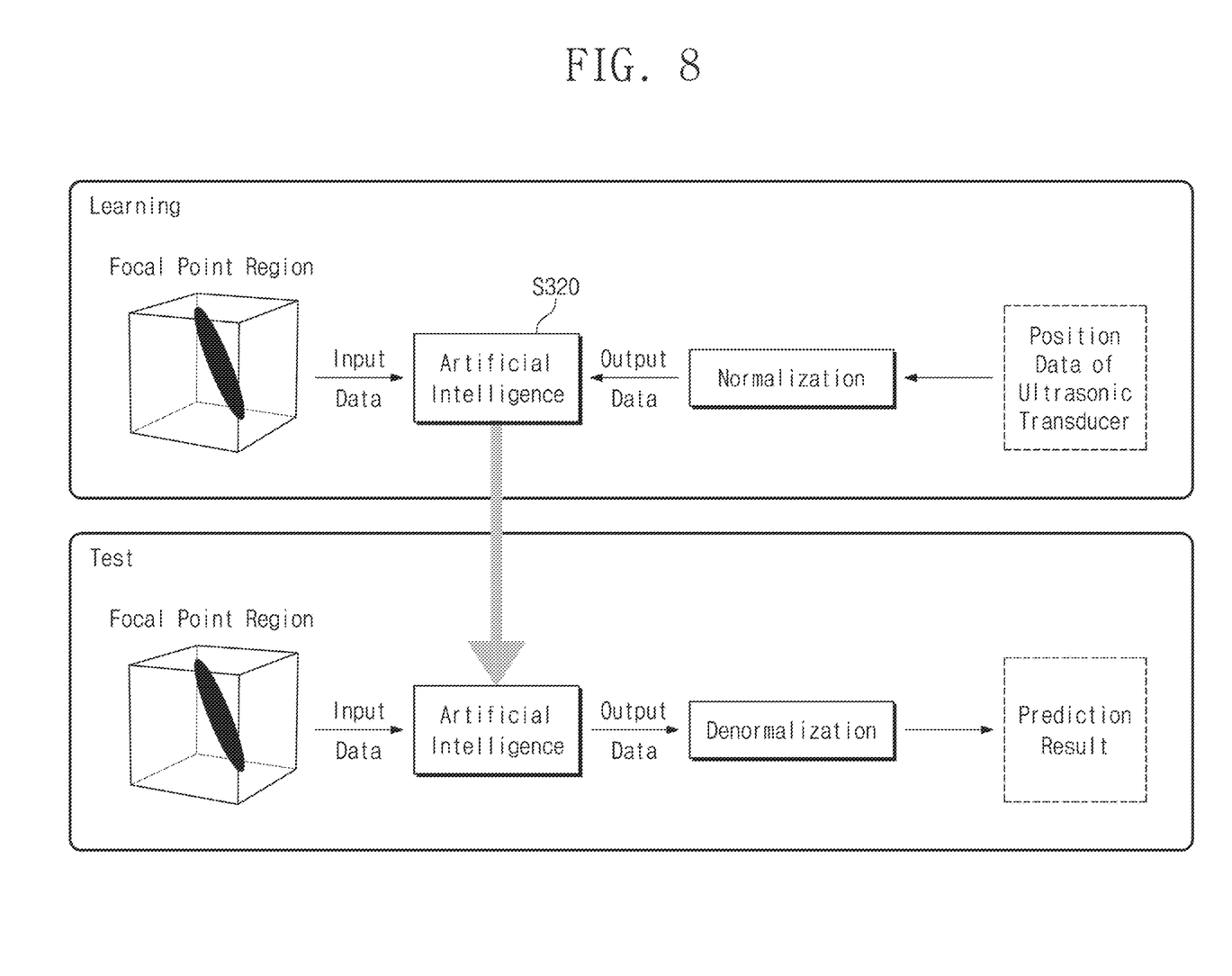
FIG. 8 is a view showing a process of allowing the ultrasonic transducer position setting artificial intelligence to perform training.

FIG. 8 is a view showing a process of allowing the ultrasonic transducer position setting artificial intelligence to perform training.

Referring to FIG. 8, the ultrasonic transducer position setting artificial intelligence may be subjected to the training through the prepared training data.

The training data may be used to perform the training so as to predict the position data of the ultrasonic transducer according to the acoustic pressure field shape data by using the acoustic pressure field shape data as an input and using the position data of the ultrasonic transducer corresponding to the input as an output.

Regarding the acoustic pressure field shape data, a part set as the focal point region may be used as an input. In this case, the focal point region may be transformed into the boundary according to the FWHM threshold, or the ellipsoid boundary acquired by transforming the boundary according to the FWHM threshold. In this case, for the training efficiency, the focal point region may preferably be in the form of the ellipsoid boundary.

The position data of the ultrasonic transducer may include the coordinate data and the angle data, and the training may be performed to predict each of the coordinate data and the angle data. In this case, for efficient training of the artificial intelligence, the coordinate data and the angle data may be converted into values between 0 and 1 through a minimum-maximum normalization process, respectively. The artificial intelligence may train through error backpropagation. After the training is performed, when a position of the focal point region at which the ultrasound is intended to be concentrated is input in response to the acoustic pressure field shape data, the artificial intelligence may output the position data of the ultrasonic transducer, which enables the ultrasound to be concentrated at the position of the focal point region. In this case, the artificial intelligence may first output the coordinate data and the angle data as primary output values in the form of the values between 0 and 1, and denormalize the primary output values to output final output values.

Figure 9:
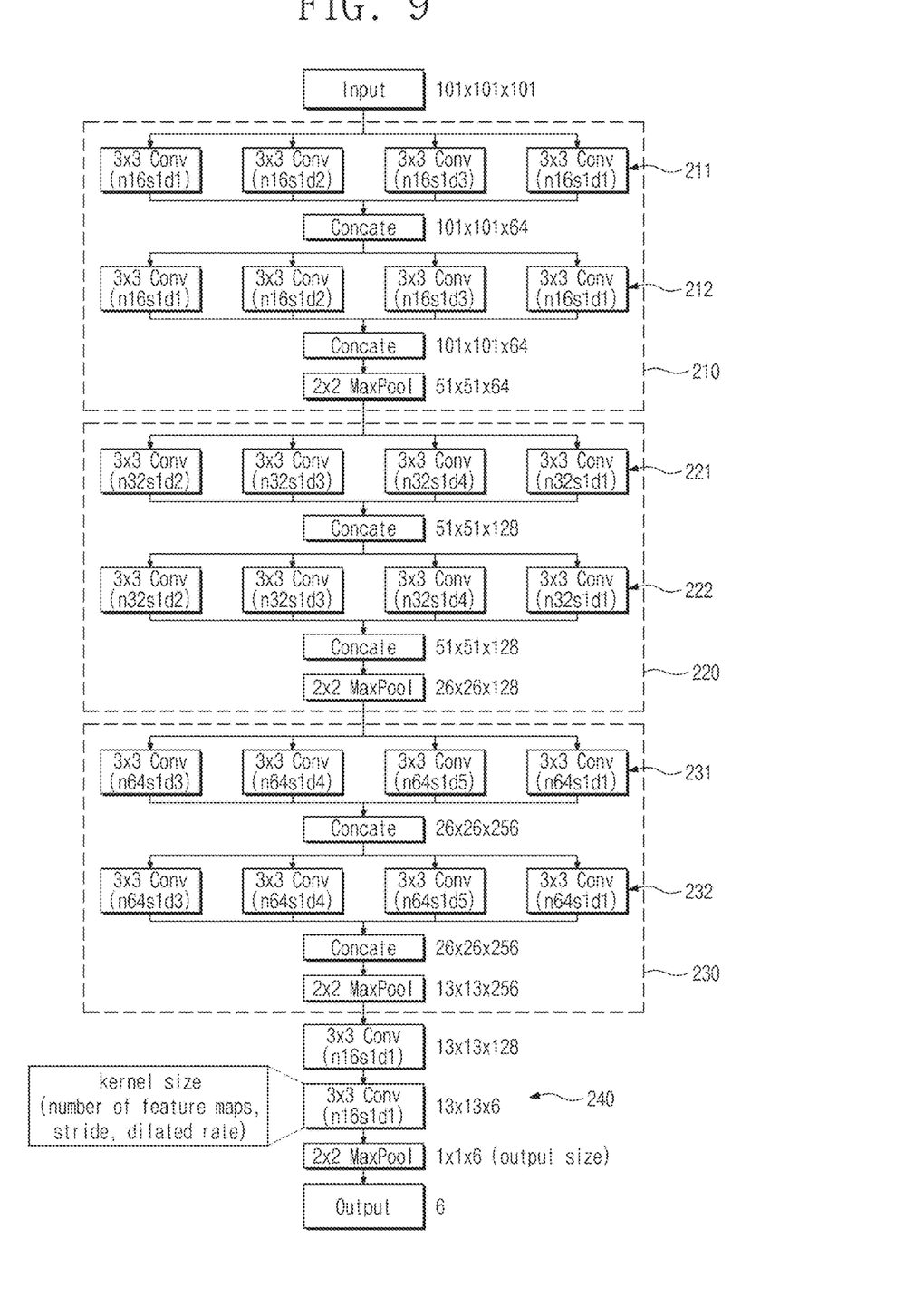
FIG. 9 is a view showing a structure of the ultrasonic transducer position setting artificial intelligence according to one embodiment of the present invention.

FIG. 9 is a view showing a structure of the ultrasonic transducer position setting artificial intelligence according to one embodiment of the present invention.

Referring to FIG. 9, according to one embodiment of the present invention, the ultrasonic transducer position setting artificial intelligence may include feature map training units 210, 220, and 230 and a coordinate training unit 240.

Each of the feature map training units 210, 220, and 230 may train a feature map from the input data. Each of the feature map training units 210, 220, and 230 may include at least one modified atrous spatial pyramid pooling module. The modified atrous spatial pyramid pooling module may include two convolutional network layers and one max pooling layer. Each of first convolutional network layers 211, 221, and 231 and second convolutional network layers 212, 222, and 232 may include four 3×3 convolutional networks connected in parallel to each other. A number n of feature maps and a stride s may be set to be the same in the convolutional networks included in each of the first convolutional network layers 211, 221, and 231. The convolutional networks included in each of the first convolutional network layers 211, 221, and 231 may have mutually different dilation rates d. Results of the convolutional networks included in each of the first convolutional network layers 211, 221, and 231 may be composed and output. In this case, ReLU may be used as an activation function. The second convolutional network layers 212, 222, and 232 may be connected to output terminals of the first convolutional network layers 211, 221, and 231, and may have the same structure as the first convolutional network layers 211, 221, and 231.

The max pooling layer may be connected to output terminals of the second convolutional network layers 212, 222, and 232. The max pooling layer may be provided as a 2×2 max pooling layer.

Preferably, each of the feature map training units 210, 220, and 230 may include three modified atrous spatial pyramid pooling modules, including a first modified atrous spatial pyramid pooling module 210, a second modified atrous spatial pyramid pooling module 220, and a third modified atrous spatial pyramid pooling module 230. In this case, the modified atrous spatial pyramid pooling module may have mutually different dilation rates of the convolutional networks constituting the convolutional network layer.

The first modified atrous spatial pyramid pooling module 210 may be configured such that dilation rates of the convolutional networks included in the first convolutional network layer 211 are 1, 2, 3, and 1, respectively. Each of the convolutional networks included in the first convolutional network layer 211 may be configured such that the number n of feature maps is 16, and the stride s is 1.

The second modified atrous spatial pyramid pooling module 220 may be connected to an output terminal of the first modified atrous spatial pyramid pooling module 210. The second modified atrous spatial pyramid pooling module 220 may be configured such that dilation rates of the convolutional networks included in the first convolutional network layer 221 are 2, 3, 4, and 1, respectively. The number n of feature maps of each of the convolutional networks included in the first convolutional network layer 221 may be two times the number n of feature maps of the convolutional network included in the first modified atrous spatial pyramid pooling module 210. The stride s of each of the convolutional networks included in the first convolutional network layer 221 may be equal to the stride s of the convolutional network included in the first modified atrous spatial pyramid pooling module 210.

The third modified atrous spatial pyramid pooling module 230 may be connected to an output terminal of the second modified atrous spatial pyramid pooling module 220. The third modified atrous spatial pyramid pooling module 230 may be configured such that dilation rates of the convolutional networks included in the first convolutional network layer 231 are 3, 4, 5, and 1, respectively. The number n of feature maps of each of the convolutional networks included in the first convolutional network layer 231 may be two times the number n of feature maps of the convolutional network included in the second modified atrous spatial pyramid pooling module 220. The stride s of each of the convolutional networks included in the first convolutional network layer 231 may be equal to the stride s of the convolutional network included in the first modified atrous spatial pyramid pooling module 210.

The coordinate training unit 240 may train a relation between the feature map and the position data of the ultrasonic transducer. The coordinate training unit 240 may include a first convolutional network layer on a coordinate training unit side, a second convolutional network layer on the coordinate training unit side, and a max pooling layer on the coordinate training unit side.

The first convolutional network layer on the coordinate training unit side may be provided as a 3×3 convolutional network. The number of feature maps of a first convolutional network on the coordinate training unit side may be equal to the number of feature maps of the convolutional network of the first modified atrous spatial pyramid pooling module 210. The first convolutional network on the coordinate training unit side may be configured such that a stride is 1, and a dilation rate is 1, and ReLU may be used as an activation function.

The second convolutional network layer on the coordinate training unit side may be provided as a 3×3 convolutional network. The second convolutional network layer on the coordinate training unit side may have the same structure as the first convolutional network layer on the coordinate training unit side.

The max pooling layer on the coordinate training unit side may be provided as a 2×2 max pooling layer.

EXPERIMENTAL EXAMPLE

Training was performed on the artificial intelligence having the structure shown in FIG. 9. In this case, data generated by creating skull models 110 by using three different actual skulls and performing a simulation for each of the skull models 110 was used as training data. Among results of the simulations for the skull models 110, 1012 results were used as the training data, and 113 results were used to test the artificial intelligence that is subjected to the training. The training data was created through an ultrasound simulation based on computational mechanics and parallel calculation using a GPU device, and about 31 hours per one skull model 110 was required for the generation of the data. The training of the artificial intelligence was performed in an Intel i9-7940X-CPU, 64.0 GB-RAM, NVIDIA GeForce 2080Ti-single GPU environment, and performed with an optimization function of Adam, an epoch of 1500, a batch size of 40, and a training rate of 0.001. A mean square error for position information of an ultrasonic transducer was used as a loss function for error backpropagation, and a function of the mean square error may be expressed as [Mathematical Formula 5] below.

$$f_{loss} = \frac{1}{n}\sum_{i=1}^{n}\left(\frac{|{}^{(i)}T_c^{pred} - {}^{(i)}T_c|^2 + |{}^{(i)}n_t^{pred} - {}^{(i)}n_t|^2}{2}\right) \quad \text{[Formula 5]}$$

In this case, n represents the number of training data, ${}^{(i)}T_c$ and ${}^{(i)}n_t$ represent coordinate data and a normal vector, which is angle data, for a position of an ultrasonic generator in $i^{th}$ data, respectively. In addition, ${}^{(i)}T_c^{pred}$ and ${}^{(i)}n_t^{pred}$ represent prediction values for coordinate data and angle data of an ultrasonic generator output from artificial intelligence being subjected to training, respectively.

In order to evaluate performance of the ultrasonic transducer position setting artificial intelligence according to one embodiment of the present invention, the following three metrics may be used.

(1) A relative error between coordinate data and angle data of an ultrasonic generator predicted by the artificial intelligence that is subjected to the training and a position and a normal vector of the ultrasonic generator corresponding to a correct answer is measured.

(2) Position data of the ultrasonic generator predicted by the artificial intelligence that is subjected to the training is input as an input of an ultrasound simulation based on computational mechanics, and an intersection-over-union (IoU) is measured to digitize a degree by which a focal point region of an acoustic pressure field output according to the input overlaps acoustic pressure field shape data used as an input of the artificial intelligence.

(3) A training time and an inference time of a model are measured to evaluate practicality of the artificial intelligence that is subjected to the training.

The first and second metrics may be digitized by using [Mathematical Formula 6], [Mathematical Formula 7], and [Mathematical Formula 8] below.

$$\Delta T_c = \frac{1}{m}\sum_{j=1}^{m}\frac{|{}^{(j)}T_c - {}^{(j)}T_c^{pred}|}{|{}^{(j)}T_c|} \quad \text{[Formula 6]}$$

$$\Delta n_t = \frac{1}{m}\sum_{j=1}^{m}\frac{|{}^{(j)}n_t - {}^{(j)}n_t^{pred}|}{|{}^{(j)}n_t|} \quad \text{[Formula 7]}$$

In this case, m is the number of experimental data to measure performance of artificial intelligence.
${}^{(j)}T_c$
and
${}^{(j)}n_t$
represent position coordinates and a normal vector for an orientation of an actual ultrasonic generator, respectively, and
${}^{(j)}T_c^{pred}$
and
${}^{(j)}n_t^{pred}$
represent prediction values for a position and an orientation of an ultrasonic generator output from artificial intelligence that has been subjected to training, respectively.

$${}^{(j)}IoU = \frac{({}^{(j)}\overline{P}_{ROI} \cap {}^{(j)}\overline{P}_{ROI}^{pred})}{({}^{(j)}\overline{P}_{ROI} \cup {}^{(j)}\overline{P}_{ROI}^{pred})} \quad \text{[Formula 8]}$$

In this case,
${}^{(j)}\overline{P}_{ROI}$
and
${}^{(j)}\overline{P}_{ROI}^{pred}$
represent acoustic pressure field shape data used as an input value to artificial intelligence and a focal point region of an acoustic pressure field predicted through a simulation, respectively.

Figure 10:
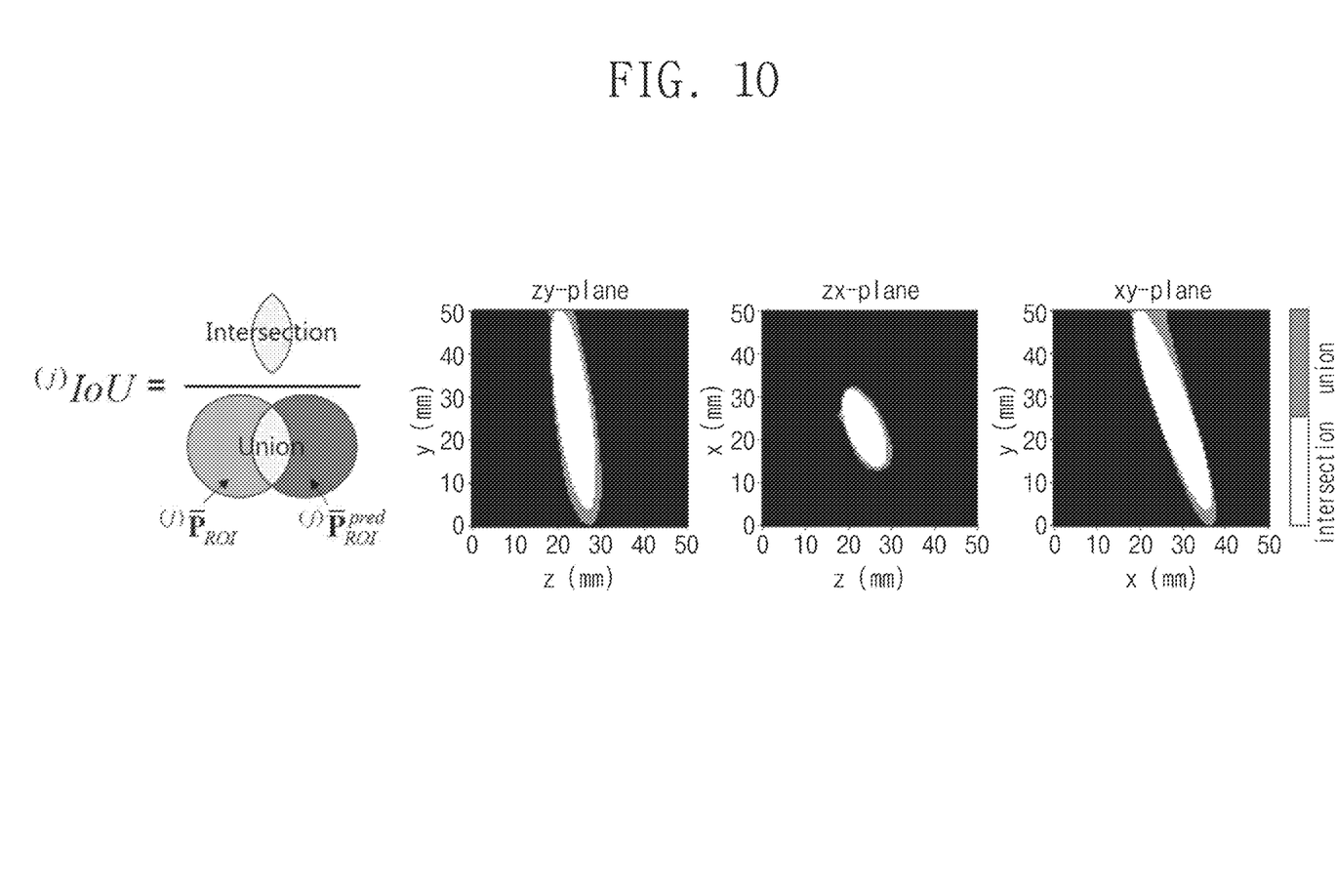
FIG. 10 is one example view that visualizes an IoU used to compare a prediction value acquired by the artificial intelligence that is subjected to the training according to the present invention with a prediction value acquired by an ultrasound simulation based on computational mechanics.

FIG. 10 is one example view that visualizes an IoU used to compare a prediction value acquired by the artificial intelligence that is subjected to the training according to the present invention with a prediction value acquired by an ultrasound simulation based on computational mechanics.

In FIG. 10, a white region represents a region in which the acoustic pressure field shape data used as an input value to the artificial intelligence and the focal point region of the acoustic pressure field predicted through the simulation coincide with each other, and a gray region represents an error region.

Tables 1 and 2 below show the performance of the artificial intelligence that is subjected to the training according to the present invention based on the measurement references described above. Table 1 shows an error in predicting a position of an ultrasonic transducer, and a training time and a prediction time of the artificial intelligence, and Table 2 shows a coincidence degree for the focal point region of the acoustic pressure field when the ultrasound is emitted at the predicted position of the ultrasonic transducer.

TABLE 1

| Skull | Difference in transducer placement | | Training time [min] | Inference time [ms] |
| --- | --- | --- | --- | --- |
| | Location ($\Delta T_c$) | Orientation($\Delta n_t$) | | |
| 'HS1' | 0.19 ± 0.19 | 0.08 ± 0.08 | 167 | 12.25 |
| 'HS2' | 0.67 ± 0.67 | 1.23 ± 0.86 | 167 | 12.25 |
| 'HS3' | 0.15 ± 0.15 | 0.11 ± 0.11 | 167 | 12.25 |

TABLE 2

| Skull | Accuracy for focal volume | |
| --- | --- | --- |
| | IoU [%] | Focal point error [mm] |
| 'HS1' | 73.82 ± 5.11 | 1.09 ± 0.71 |
| 'HS2' | 75.85 ± 5.85 | 0.81 ± 0.49 |
| 'HS3' | 73.79 ± 4.85 | 0.97 ± 0.52 |

Figure 11:
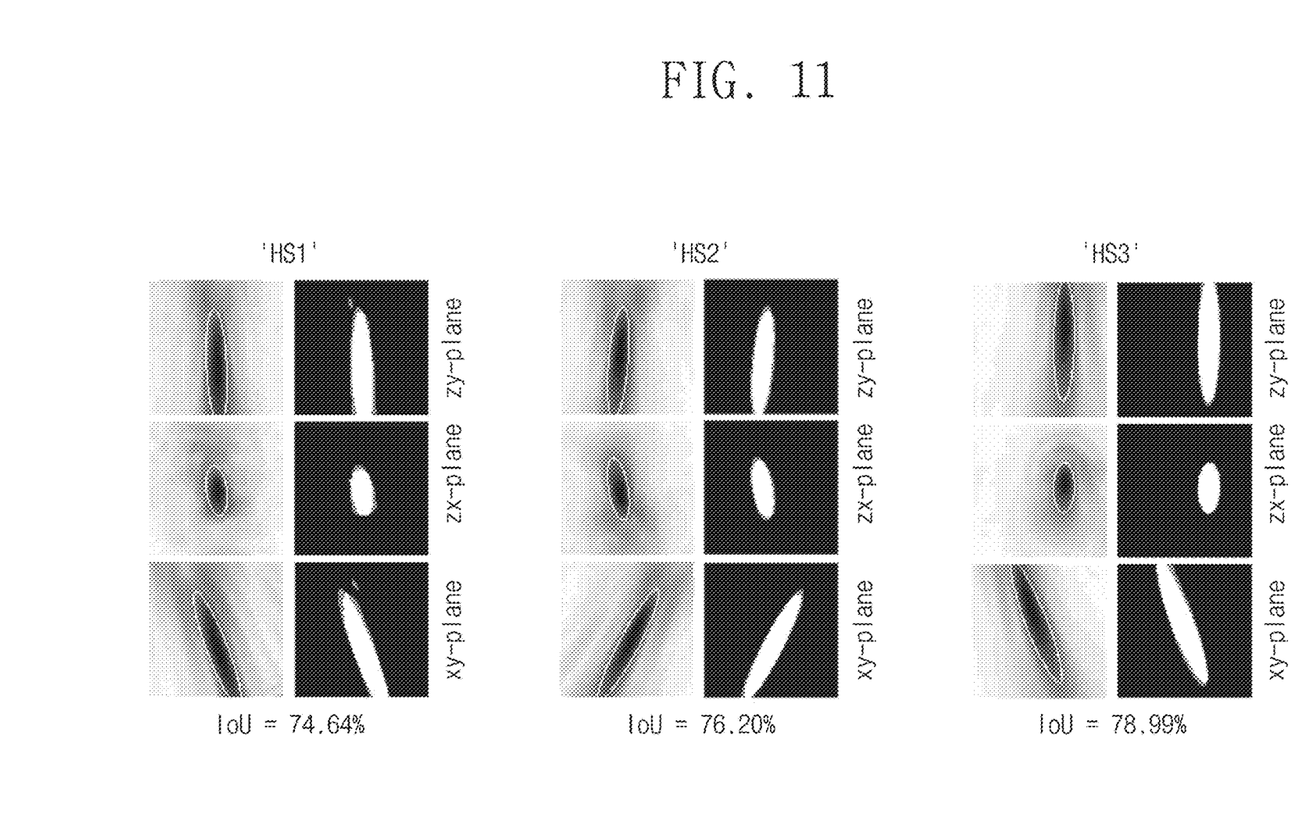
FIG. 11 is a view that compares a focal point region of ultrasound predicted by an experimental example of the present invention with a focal point region of ultrasound predicted by the simulation.

As shown in Table 1, the ultrasonic transducer position setting artificial intelligence according to one embodiment of the present invention exhibits high accuracy with an error rate of 0.34±0.24% in predicting the position of the ultrasonic transducer ($\Delta T_c$) and an error rate of 0.47±0.54% in predicting the normal vector ($\Delta n_t$). Additionally, as shown in Table 2, the ultrasonic transducer position setting artificial intelligence according to one embodiment of the present invention exhibits performance with an average IoU of 73% or more and a standard deviation of about 5% in predicting the region of interest 150 of the acoustic pressure field, and exhibits a very small error of 0.96 mm on average in predicting the focal point of the acoustic pressure field. FIG. 11 is a view that compares a focal point region of ultrasound predicted by an experimental example of the present invention with a focal point region of ultrasound predicted by the simulation.

HS1, HS2, and HS3 represent the results for the skull models 110 implemented through the different actual skulls, respectively. In three pairs of drawings, three drawings on a left side show the acoustic pressure field shape data used as the input data of the artificial intelligence and the acoustic pressure field, which is a result of performing a simulation by positioning the ultrasonic transducer on the output data acquired by the artificial intelligence. In the three pairs of drawings, three pictures on a right side are acquired by visualizing the IoU to check a degree by which the focal point regions coincide with each other. It was found that the acoustic pressure field shape data used as the input data of the artificial intelligence and a shape of the acoustic pressure field output by the simulation match each other with high accuracy.

An existing computational dynamics-based focused ultrasound simulation requires about 100 seconds for each acoustic pressure field to model the acoustic pressure field in the region of interest according to the input of the position information of the ultrasonic transducer, and requires 31 hours to generate all the training data. Meanwhile, the ultrasonic transducer position setting artificial intelligence according to one embodiment of the present invention requires about 167 minutes for network training, and requires 12.25 ms to output the position data of the ultrasonic transducer according to the input data. Accordingly, it was found that the ultrasonic transducer position setting artificial intelligence according to one embodiment of the present invention is capable of performing an inverse operation of the existing computational dynamics-based focused ultrasound simulation with high accuracy, and performing real-time prediction within approximately 10 ms.

Although the exemplary embodiments of the present invention have been described in detail above, the scope of the present invention is not limited to a specific embodiment, and shall be interpreted by the appended claims. In addition, it is to be understood by those of ordinary skill in the art that various changes and modifications can be made without departing from the scope of the present invention.

The invention claimed is:

1. An ultrasonic transducer position setting device comprising:
   an input/output unit for allowing a user to input data, and outputting the data in a form that is recognizable by the user;
   a memory for storing an ultrasonic transducer position setting program; and
   a control unit for executing the ultrasonic transducer position setting program to derive result data according to the data input through the input/output unit,
   wherein, when a focal point position of ultrasound, which is set to a region where a brain is positioned inside a skull in a living body, is input, the control unit outputs position data of an ultrasonic transducer, which allows the ultrasound to be applied to the input focal point position of the ultrasound, and
   wherein the ultrasonic transducer position setting program is provided by artificial intelligence based on a deep neural network (DNN) and includes a feature map training unit for training a feature map from the input data,
   wherein the feature map training unit includes at least one modified atrous spatial pyramid pooling module, and
   wherein the feature map training unit includes:
      a first modified atrous spatial pyramid pooling module;
      a second modified atrous spatial pyramid pooling module connected to an output terminal of the first modified atrous spatial pyramid pooling module; and
      a third modified atrous spatial pyramid pooling module connected to an output terminal of the second modified atrous spatial pyramid pooling module.

2. The ultrasonic transducer position setting device of claim 1, wherein the control unit outputs the position data of the ultrasonic transducer, which enables the ultrasound to be concentrated at the input focal point position, by reflecting that refraction occurs as the ultrasound passes through the skull.

3. The ultrasonic transducer position setting device of claim 2, wherein the position data of the ultrasonic transducer includes coordinate data representing three-dimensional coordinates at which the ultrasonic transducer is positioned with respect to the skull, and angle data representing an angle at which the ultrasonic transducer is positioned with respect to the skull.

4. The ultrasonic transducer position setting device of claim 1, wherein the ultrasonic transducer position setting program includes:
   a coordinate training unit for training a relation between the feature map and the position data of the ultrasonic transducer.

5. The ultrasonic transducer position setting device of claim 1, wherein the at least one modified atrous spatial pyramid pooling module includes:
   a first convolutional network layer;
   a second convolutional network layer connected to an output terminal of the first convolutional network layer; and a max pooling layer connected to an output terminal of the second convolutional network layer.

6. The ultrasonic transducer position setting device of claim 5, wherein the first convolutional network layer includes four convolutional networks connected in parallel to each other.

7. The ultrasonic transducer position setting device of claim 6, wherein the second convolutional network layer includes four convolutional networks connected in parallel to each other.

8. The ultrasonic transducer position setting device of claim 1, wherein the first modified atrous spatial pyramid pooling module, the second modified atrous spatial pyramid pooling module, and the third modified atrous spatial pyramid pooling module have mutually different dilation rates of convolutional networks.

9. The ultrasonic transducer position setting device of claim 1, wherein the artificial intelligence uses training data including shape data of the skull, the position data of the ultrasonic transducer, and acoustic pressure field shape data to perform training so as to predict the position data of the ultrasonic transducer according to the acoustic pressure field shape data by using the acoustic pressure field shape data as an input and using the position data of the ultrasonic transducer corresponding to the input as an output.

10. The ultrasonic transducer position setting device of claim 9, wherein the training data is generated through a simulation based on computational mechanics.

11. An ultrasonic transducer position setting program, wherein the ultrasonic transducer position setting program is stored in a recording medium that is readable by an ultrasonic transducer position setting device in order to allow the ultrasonic transducer position setting device to execute:
inputting a focal point position of ultrasound, which is set to a region where a brain is positioned inside a skull in a living body; and
outputting position data of an ultrasonic transducer, which allows the ultrasound to be applied to the input focal point position of the ultrasound,
wherein the ultrasonic transducer position setting program is provided by artificial intelligence based on a deep neural network (DNN) and includes a feature map training unit for training a feature map from the input data,
wherein the feature map training unit includes at least one modified atrous spatial pyramid pooling module, and
wherein the feature map training unit includes:
a first modified atrous spatial pyramid pooling module;
a second modified atrous spatial pyramid pooling module connected to an output terminal of the first modified atrous spatial pyramid pooling module; and
a third modified atrous spatial pyramid pooling module connected to an output terminal of the second modified atrous spatial pyramid pooling module.

12. The ultrasonic transducer position setting program of claim 11, wherein the position data of the ultrasonic transducer includes coordinate data representing three-dimensional coordinates at which the ultrasonic transducer is positioned with respect to the skull, and angle data representing an angle at which the ultrasonic transducer is positioned with respect to the skull.

13. A method for implementing ultrasonic transducer position setting artificial intelligence, which is provided by an ultrasonic transducer position setting program stored in a recording medium that is readable by an ultrasonic transducer position setting device, the method comprising:
preparing training data including shape data of a skull, position data of an ultrasonic transducer, and acoustic pressure field shape data; and
allowing artificial intelligence to perform training so as to predict the position data of the ultrasonic transducer according to the acoustic pressure field shape data by using the acoustic pressure field shape data as an input and using the position data of the ultrasonic transducer corresponding to the input as an output in the training data,
wherein the ultrasonic transducer position setting program is provided by artificial intelligence based on a deep neural network (DNN) and includes a feature map training unit for training a feature map from the input data,
wherein the feature map training unit includes at least one modified atrous spatial pyramid pooling module, and
wherein the feature map training unit includes:
a first modified atrous spatial pyramid pooling module;
a second modified atrous spatial pyramid pooling module connected to an output terminal of the first modified atrous spatial pyramid pooling module; and
a third modified atrous spatial pyramid pooling module connected to an output terminal of the second modified atrous spatial pyramid pooling module.

\* \* \* \* \*